(12) United States Patent
Iijima (10) Patent No.: US 8,987,513 B2
(45) Date of Patent: Mar. 24, 2015

(54) OPERATION METHOD OF UREA PRODUCTION PLANT INCLUDING MULTIPLE SYSTEMS

(75) Inventor: Masaki Iijima, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/352,199

(22) PCT Filed: Dec. 15, 2011

(86) PCT No.: PCT/JP2011/079098
§ 371 (c)(1),
(2), (4) Date: Apr. 16, 2014

(87) PCT Pub. No.: WO2013/088564
PCT Pub. Date: Jun. 20, 2013

(65) Prior Publication Data
US 2014/0275626 A1    Sep. 18, 2014

(51) Int. Cl.
*C07C 273/04* (2006.01)
*C01C 1/04* (2006.01)

(52) U.S. Cl.
CPC .............. *C07C 273/04* (2013.01); *C01C 1/0488* (2013.01); *C01C 1/0482* (2013.01)
USPC .......................................................... 564/67

(58) Field of Classification Search
USPC ........................................................... 564/67
See application file for complete search history.

(56) References Cited

U.S. PATENT DOCUMENTS

| | | | |
|---|---|---|---|
| 4,320,103 A | 3/1982 | Pagani | |
| 6,342,632 B1 | 1/2002 | Pagani et al. | |
| 6,632,846 B2 * | 10/2003 | Sheppard et al. | 518/715 |
| 2006/0270872 A1 | 11/2006 | Kojima | |

FOREIGN PATENT DOCUMENTS

| | | |
|---|---|---|
| CN | 101659633 A | 3/2010 |
| JP | 51-118725 A | 10/1976 |
| JP | 10-503526 A | 3/1998 |
| JP | 2000-159519 A | 6/2000 |
| JP | 2006-335653 A | 12/2006 |

OTHER PUBLICATIONS

International Search Report, dated Feb. 7, 2012, issued in corresponding application No. PCT/JP2011/079098.
A Final Brochure, "The 2nd Annual GPCA Ferilizer Convention", Growth in Volatile Markets, Sep. 19-21, 2011, Organised by GPCA.
Iijima, Masaki, "Keeping your Urea Plant Operational when the Ammonia Plant is Down", 2nd Annual GPCA Fertilizer Convention, Sep. 20, 2011, Mitsubishi Heavy Industries.
English Translation of Written Opinion of the International Searching Authority dated Feb. 7, 2012, issued in corresponding Application No. PCT/JP2011/079098. (5 pages).
Japanese Office Action dated Dec. 24, 2014, issued in Corresponding Japanese Patent Application No. 2013-549033; w/English Translation. (5 pages).
Notice of Acceptance dated Jan. 23, 2015, issued in Australian Patent Application No. 2011383480. (2 pages).

* cited by examiner

*Primary Examiner* — Brian J Davis
(74) *Attorney, Agent, or Firm* — Westerman, Hattori, Daniels & Adrian, LLP (57) ABSTRACT

An operation method of a urea production plant including multiple systems that can prevent a considerable decrease in urea production even when an ammonia synthesis facility is shut down. At a time of producing urea from $CO_2$ and ammonia, in a case where urea production plants including at least two systems are arranged in parallel, when an ammonia production facility (10A) of one of the systems is shut down, liquefied ammonia stored in the shut down system is used, and a $CO_2$ recovery amount in a $CO_2$ recovery facility (23) in an ammonia synthesis facility (10B) of the other system is increased. Synthesis of urea can be then continued by a urea synthesis unit ($30A_1$) in the shut down system by using the increased recovered $CO_2$ and the liquefied ammonia.

1 Claim, 12 Drawing Sheets

OPERATION METHOD OF UREA PRODUCTION PLANT INCLUDING MULTIPLE SYSTEMS

FIELD

The present invention relates to an operation method of a urea production plant including multiple systems.

BACKGROUND

To produce urea, in general, ammonia ($NH_3$) obtained by using natural gas and the like as a raw material by an ammonia synthesis facility and carbon dioxide ($CO_2$) separated at the time of ammonia synthesis are used to synthesize urea ($CH_4N_2O$) by a urea synthesis unit (Patent Literature 1).

CITATION LIST

Patent Literature

Patent Literature 1: Japanese Patent Application Laid-open No. 2000-159519

SUMMARY

Technical Problem

Meanwhile, in a urea production plant that synthesizes ammonia and urea from natural gas and the like, if an ammonia synthesis facility is shut down, one week or more is normally necessary to resume operations of the facility.

As a result, if it happens, the urea production amount of the facility in the year decreases. If shutdown of the ammonia synthesis facility occurs many times throughout the year, a considerable decrease in the urea production amount occurs throughout the year. Therefore, there has been desired a method of increasing the urea production amount.

The present invention has been achieved to solve the above problem, and an object of the present invention is to provide an operation method of a urea production plant including multiple systems that can prevent a considerable decrease in urea production even when a ammonia synthesis facility is shut down.

Solution to Problem

According to an aspect of the present invention, an operation method of a urea production plant including multiple systems, at a time of producing urea by using a urea synthesis plant that includes: an ammonia synthesis facility including a reforming device having a reforming furnace that reforms natural gas to hydrogen ($H_2$) and carbon monoxide (CO) by using water vapor, a CO-shift converter that converts carbon monoxide (CO) in reformed gas to carbon dioxide, a carbon-dioxide removal device that removes obtained carbon dioxide ($CO_2$) in the reformed gas, a synthesis gas compressor that compresses synthesis material gas containing hydrogen and nitrogen, from which carbon dioxide has been removed by the carbon-dioxide removal device, and an ammonia synthesis reactor that synthesizes ammonia from compressed synthesis material gas; a liquefied ammonia storage facility that branches ammonia obtained by the ammonia synthesis reactor from an ammonia supply line for supplying ammonia to a urea synthesis unit and stores a part of synthesized ammonia in a liquefied state; a carbon-dioxide recovery facility that recovers carbon dioxide in fuel flue gas from the reforming furnace; and a carbon-dioxide supply line for supplying the removed carbon dioxide (removed $CO_2$) and the recovered carbon dioxide (recovered $CO_2$) to a urea synthesis unit, comprising: providing at least two systems of the urea synthesis plants; storing a predetermined amount of obtained ammonia in a liquefied state in the liquefied ammonia storage facility; when a trouble occurs in the ammonia synthesis facility of one of the systems and production of ammonia is stopped, temporarily supplying carbon dioxide (recovered $CO_2$) recovered by the other system to a $CO_2$ supply line of the shut down system via an emergency $CO_2$ supply line in order to supply the temporarily supplied $CO_2$ to the urea synthesis unit; supplying a predetermined amount of liquefied ammonium stored in the shut down system from an ammonia supply line to the urea synthesis unit; producing urea by using the temporarily supplied $CO_2$ and stored liquefied ammonia even in the shut down system, thereby enabling to perform a continuous operation when the ammonia synthesis facility is shut down. Advantageously, in the operation method of a urea production plant including multiple systems, the carbon dioxide recovery facility recovers recovered $CO_2$ to a maximum extent.

Advantageous Effects of Invention

According to the present invention, at the time of producing urea from $CO_2$ and ammonia, in a case where urea production plants including at least two systems are arranged in parallel, when an ammonia production facility of one of the systems is shut down, liquefied ammonia stored in the shut down system is used, and a $CO_2$ recovery amount in a $CO_2$ recovery facility in the ammonia synthesis facility of the other system is increased. Synthesis of urea can be continued even in the shut down system by using the increased recovered $CO_2$ and the liquefied ammonia.

As a result, operations of the remaining one of the two systems are normally performed to synthesize urea, and urea synthesis can be continued until restart even in the urea production plant of the one system, which has been conventionally shut down, thereby enabling to avoid a considerable decrease in a production amount throughout the year.

DESCRIPTION OF EMBODIMENTS

The present invention will be explained below in detail with reference to the accompanying drawings. The present invention is not limited the following embodiments, and configurations achieved by combining these embodiments are also included in the present invention. In addition, constituent elements in the following embodiments include those that can be easily anticipated by persons skilled in the art or that are substantially equivalent.

First Embodiment

Figure 1:
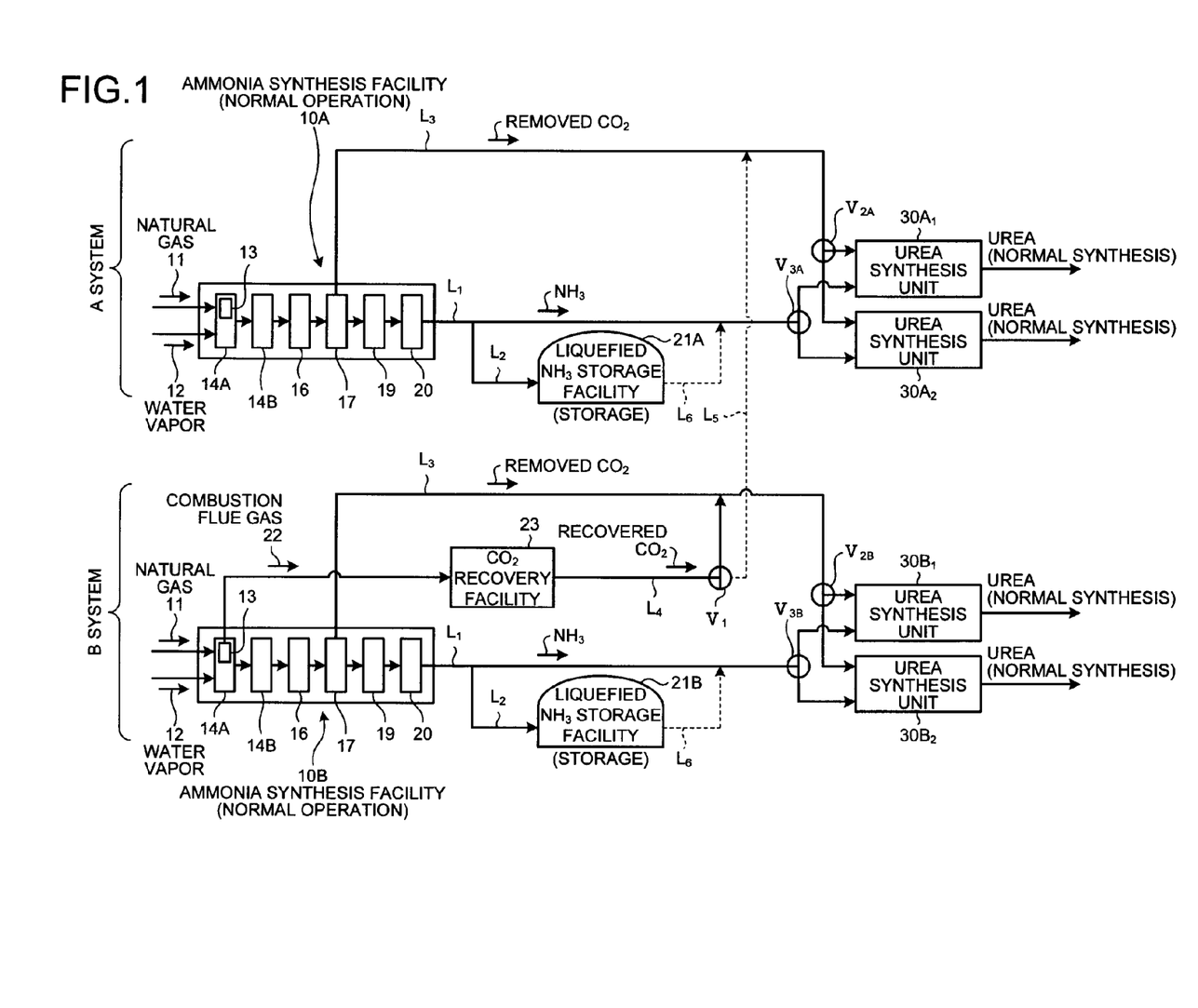
FIG. 1 is a schematic diagram of a urea production plant including multiple systems according to a first embodiment (in a normal operation state).
Figure 2:
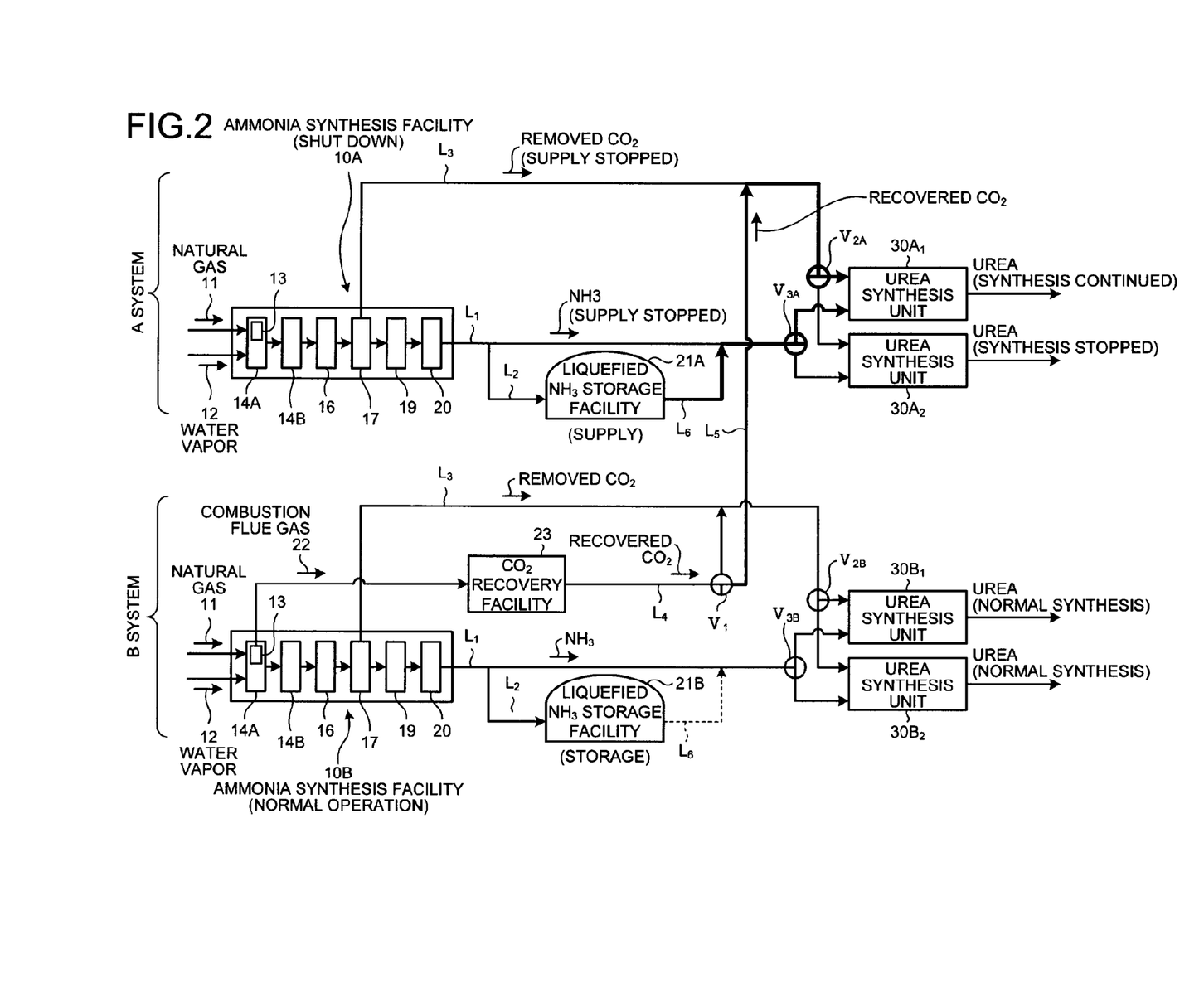
FIG. 2 is a schematic diagram of the urea production plant including multiple systems according to the first embodiment (in a state where one system is shut down).
Figure 3:
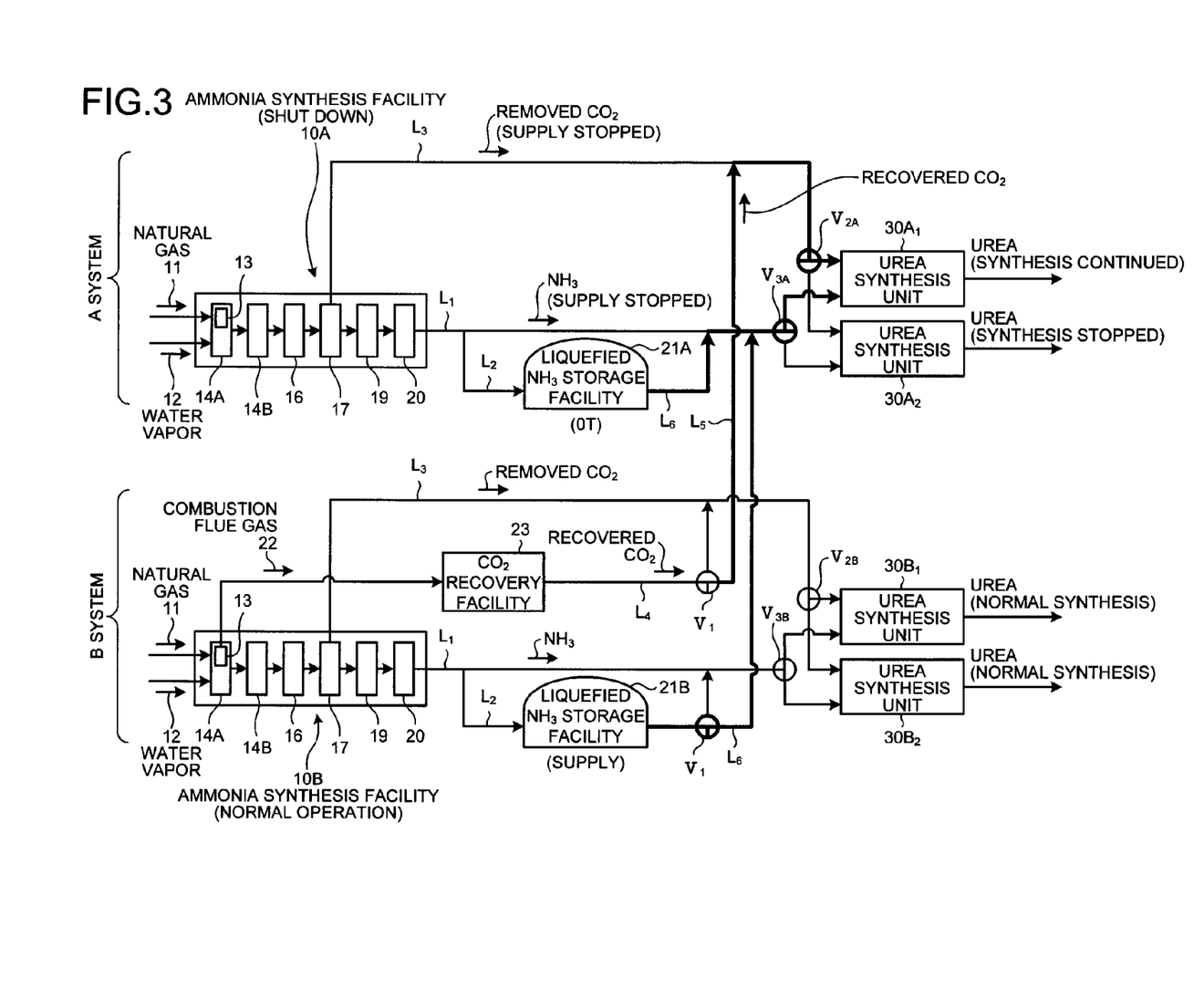
FIG. 3 is a schematic diagram of another urea production plant including multiple systems according to the first embodiment (in a state where one system is shut down).
Figure 12:
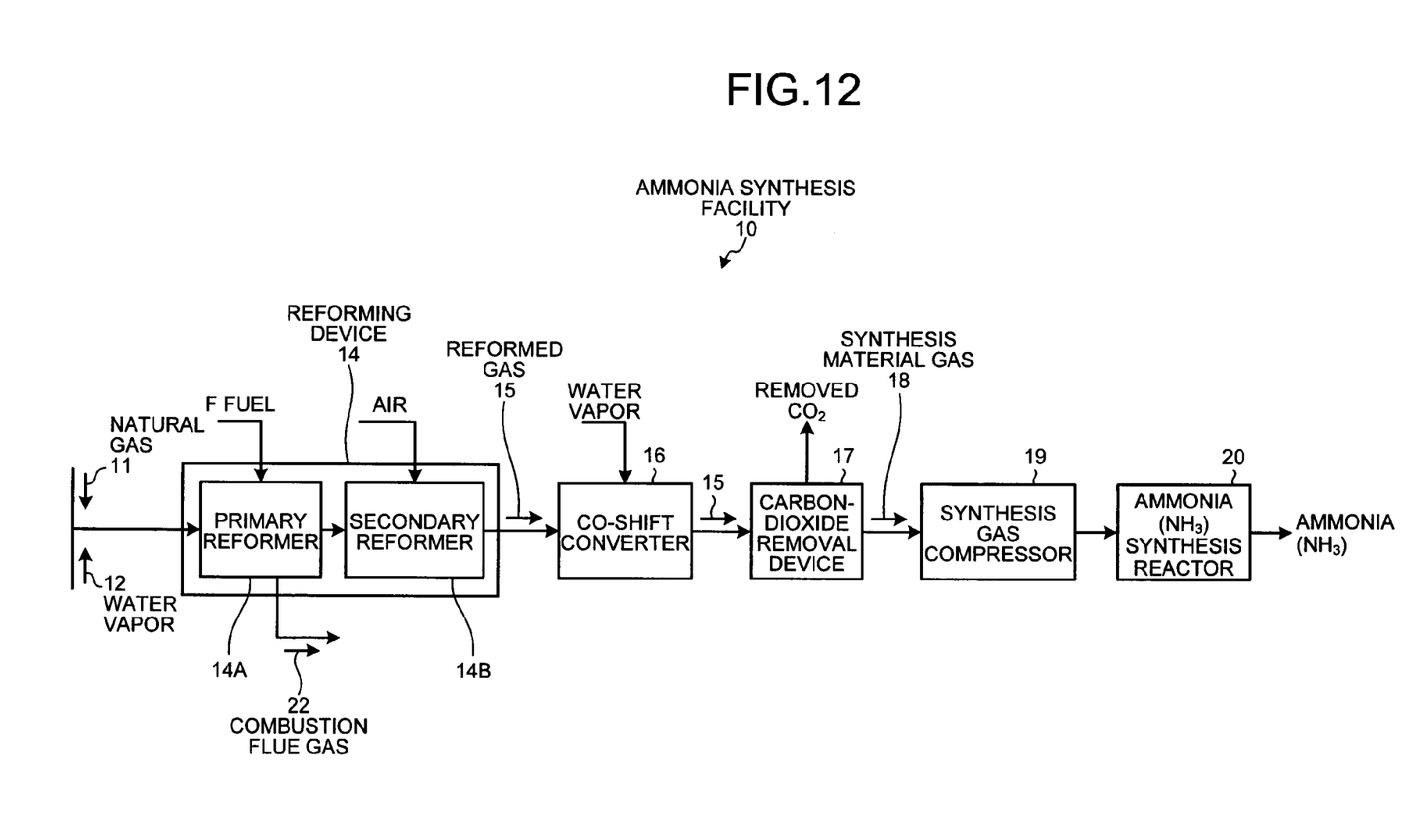
FIG. 12 is a schematic diagram of an ammonia synthesis facility according to the first embodiment.

An operation method of a urea production plant including multiple systems according to an embodiment of the present invention is explained with reference to the drawings. FIG. 1 is a schematic diagram of a urea production plant including multiple systems according to a first embodiment (in a normal operation state). FIG. 2 is a schematic diagram of the urea production plant including multiple systems according to the first embodiment (in a state where one system is shut down). FIG. 3 is a schematic diagram of another urea production plant including multiple systems according to the first embodiment (in a state where one system is shut down). FIG. 12 is a schematic diagram of an ammonia synthesis facility according to the first embodiment. In the present embodiment, as shown in FIG. 1, a parallel-type urea production plant is provided in which urea is produced, respectively, by two systems of an ammonia synthesis facility 10A and an ammonia synthesis facility 10B.

An example of the ammonia synthesis facility that produces a raw material for urea production is explained first with reference to FIG. 12.

As shown in FIG. 12, an ammonia synthesis facility 10 includes a reforming device 14 having a reforming furnace 13 that reforms natural gas 11 to hydrogen ($H_2$) and carbon monoxide (CO) by using water vapor 12, a CO-shift converter 16 that converts carbon monoxide (CO) in reformed gas 15 to carbon dioxide, a carbon-dioxide removal device 17 that removes obtained carbon dioxide ($CO_2$) in the reformed gas 15, a synthesis gas compressor 19 that compresses synthesis material gas 18 containing hydrogen and nitrogen, in which carbon dioxide has been removed by the carbon-dioxide removal device 17, and an ammonia synthesis reactor 20 that synthesizes ammonia from the compressed synthesis material gas.

The reforming device 14 produces hydrogen by reforming the natural gas 11, and includes a primary reformer 14A and a secondary reformer 14B. In primary reforming, the water vapor 12 is added to the natural gas 11, to reform the most part of methane. Air is added thereto by an amount of nitrogen corresponding to the generated hydrogen amount to perform secondary reforming.

The CO-shift converter 16 first converts CO to $CO_2$ in order to remove carbon, thereby obtaining the reformed gas 15.

The carbon-dioxide removal device 17 removes carbon dioxide ($CO_2$), which is then regenerated as $CO_2$ having a high purity for a raw material of urea.

In the synthesis material gas 18 in which $CO_2$ has been removed, a hydrogen to nitrogen ratio is 3:1, and the pressure of the synthesis material gas 18 is raised to a high pressure required for synthesis by the synthesis gas compressor 19.

The ammonia synthesis reactor 20 synthesizes ammonia ($NH_3$) from hydrogen and nitrogen.

Fuel F is supplied to the reforming furnace 13 in the primary reformer 14A of the reforming device 14, so that combustion flue gas 22 generated thereby is discharged to outside. $CO_2$ contained in the combustion flue gas 22 is recovered by a $CO_2$ recovery facility 23 as described below.

The urea production plant of one system (an A system) in FIG. 1 supplies ammonia obtained by the ammonia synthesis reactor 20 in the ammonia synthesis facility 10A and $CO_2$ removed by the $CO_2$ removal device 17 (removed $CO_2$) to a urea synthesis unit 30 (urea synthesis units $30A_1$ and $30A_2$), where urea is synthesized by the urea synthesis units $30A_1$ and $30A_2$ (normal synthesis).

A urea production plant of the other system (a B system) in FIG. 1 supplies ammonia obtained by the ammonia synthesis reactor 20 in the ammonia synthesis facility 10B and $CO_2$ removed by the $CO_2$ removal device 17 (removed $CO_2$) to the urea synthesis unit 30 (urea synthesis units $30B_1$ and $30B_2$), where urea is synthesized by the urea synthesis units $30B_1$ and $30B_2$ (normal synthesis).

A $CO_2$ recovery facility 23 that recovers $CO_2$ in the combustion flue gas 22 discharged from the primary reformer 14A in the ammonia synthesis facility 10B is installed in the urea production plant of the B system (a lower stage).

In FIG. 1, reference sign $L_1$ denotes an ammonia supply line, $L_2$ denotes an ammonia storage line, $L_3$ denotes a removed $CO_2$ supply line, $L_4$ denotes a recovered $CO_2$ supply line, $L_5$ denotes an emergency $CO_2$ supply line, $L_6$ denotes an ammonia supply line, $V_1$ denotes a recovered $CO_2$ supply valve, $V_{2A}$ and $V_{2B}$ denote a removed $CO_2$ supply valve, and $V_{3A}$ and $V_{3B}$ denote an ammonia supply valve.

Further, liquefied $NH_3$ storage facilities 21A and 21B that can store a predetermined amount of ammonia obtained from the respective systems (the A system and the B system) in a liquefied state are installed.

In such facilities, at the time of a normal operation, ammonia is synthesized by the ammonia synthesis facilities 10A and 10B of the A system and the B system, and urea is synthesized from ammonia and $CO_2$, respectively, by the urea synthesis units $30A_1$, $30A_2$, $30B_1$, and $30B_2$, by using removed $CO_2$ removed from the ammonia synthesis facilities 10A and 10B.

In the B system, because recovered $CO_2$ recovered by the $CO_2$ recovery facility 23 can be supplied for urea synthesis, a total amount of urea synthesis in the urea synthesis unit of the B system can be increased than that of the urea synthesis unit of the A system.

In the urea production facility, such a plurality of systems are operated in parallel, so that urea is produced continuously throughout the year to ensure a predetermined annual production amount.

Meanwhile, in the ammonia synthesis facility, when a failure (such as trip of ancillary facilities) occurs in the facility or power supply is stopped, one week or more is normally necessary to resume operations. This is because the ammonia synthesis facility is formed by a combination of devices in a plurality of processes and the reforming furnace 13 is operated in a high temperature condition, therefore, if the ammonia synthesis facility is shut down once, a certain period of time (at least one week) is required for raising the temperature and pressure and for stabilization.

Therefore, in the present invention, even in the period until restart (at least one week), urea can be produced stably.

As shown in FIG. 2, when ammonia synthesis in the A system is stopped, carbon dioxide (recovered $CO_2$) recovered by the other system (for example, the B system) is temporarily supplied to the removed $CO_2$ supply line $L_3$ of the shut down system (the A system) via the emergency $CO_2$ supply line $L_5$ (the thick line in FIG. 2). The temporarily supplied recovered $CO_2$ is supplied by switching the removed $CO_2$ supply valve $V_{2A}$ to the urea synthesis unit 30A₁ side.

Liquefied ammonium stored in the liquefied $NH_3$ storage facility 21A in the ammonia synthesis facility 10A of the shut down system (the A system) is supplied from the ammonia supply line $L_1$ by switching the $NH_3$ supply valve $V_{3A}$ to the urea synthesis unit 30A₁ side.

As a result, even in the shut down system (the A system), urea can be produced in the urea synthesis unit 30A₁ by using the temporarily supplied $CO_2$ and the stored liquefied ammonia.

Accordingly, in the ammonia synthesis facility 10A of the A system, even if supply of removed $CO_2$ is stopped due to shutdown of the ammonia synthesis facility, recovered $CO_2$ is supplied from the B system via the emergency $CO_2$ supply line (the thick line in FIG. 2) $L_5$, thereby enabling to perform ammonia synthesis continuously.

As an amount to be stored in the liquefied $NH_3$ storage facility 21A, an amount for at least one week, which is required for resuming operations in the shut down ammonia synthesis facility 10A, needs only to be stored in a liquefied state.

Further, it is desired that the $CO_2$ recovery facility 23 in the B system has a size more sufficient than a $CO_2$ recovery amount of a general $CO_2$ recovery facility (four to five times the size of a general size).

Furthermore, the recovered $CO_2$ can be supplied to the A system side by recovering $CO_2$ to a maximum extent (recovery efficiency: 90%) at the time of shutdown of one plant.

As a result, a decrease in the urea production amount throughout the year can be prevented, and a problem of considerable decrease in the urea production amount occurring throughout the year can be resolved, thereby enabling to stabilize urea production.

This is advantageous because urea is an important material as a fertilizer; stable production thereof throughout the year is desired.

Furthermore, as shown in FIG. 3, when the operation of the ammonia synthesis facility 10A of the A system is not resumed even if all of the liquefied ammonium stored in the liquefied $NH_3$ storage facility 21A of the A system has been consumed, liquefied ammonium in the liquefied $NH_3$ storage facility 21B of the B system can be supplied to the ammonia supply line $L_1$ on the A system side via the ammonia supply line $L_6$, so that a continuous operation of urea synthesis for one more week can be performed.

Figure 4:
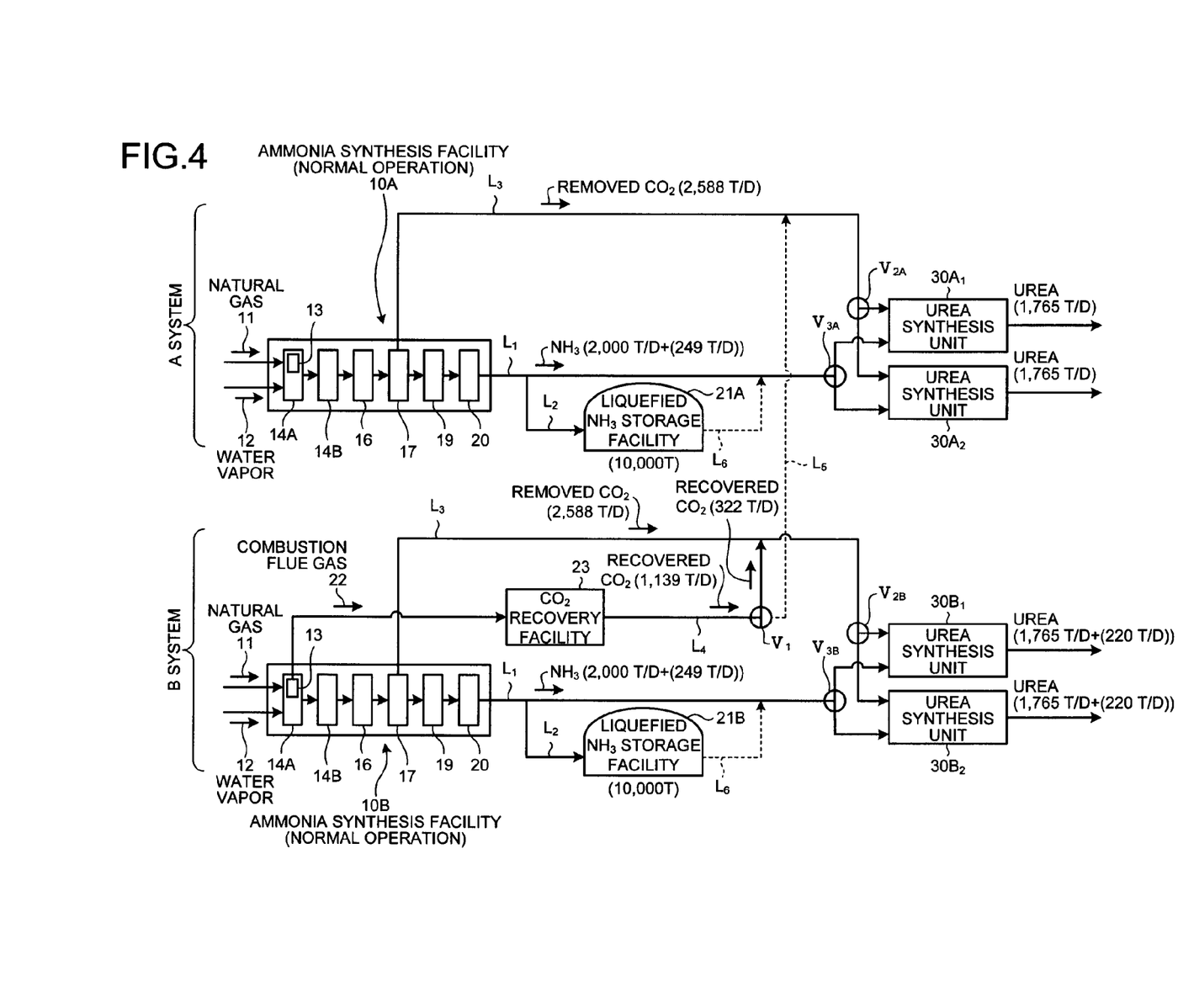
FIG. 4 is a schematic diagram of the urea production plant including multiple systems according to the first embodiment with a production amount added thereto (in a normal operation state).

In FIG. 4, which corresponds to FIG. 1, examples of an ammonia production amount, a removed $CO_2$ amount, a recovered $CO_2$ amount, a liquefied $NH_3$ amount, and a urea production amount in the normal operation are shown.

As shown in FIG. 4, production of 1,765 T/D is performed respectively in the urea synthesis units 30A₁ and 30A₂, and the urea synthesis units 30B₁ and 30B₂. The urea amount of 220 T/D in brackets in the B system is a production amount at the time of using recovered $CO_2$.

Consequently, in this plant, urea production of up to 7,500 T/D is possible.

Figure 5:
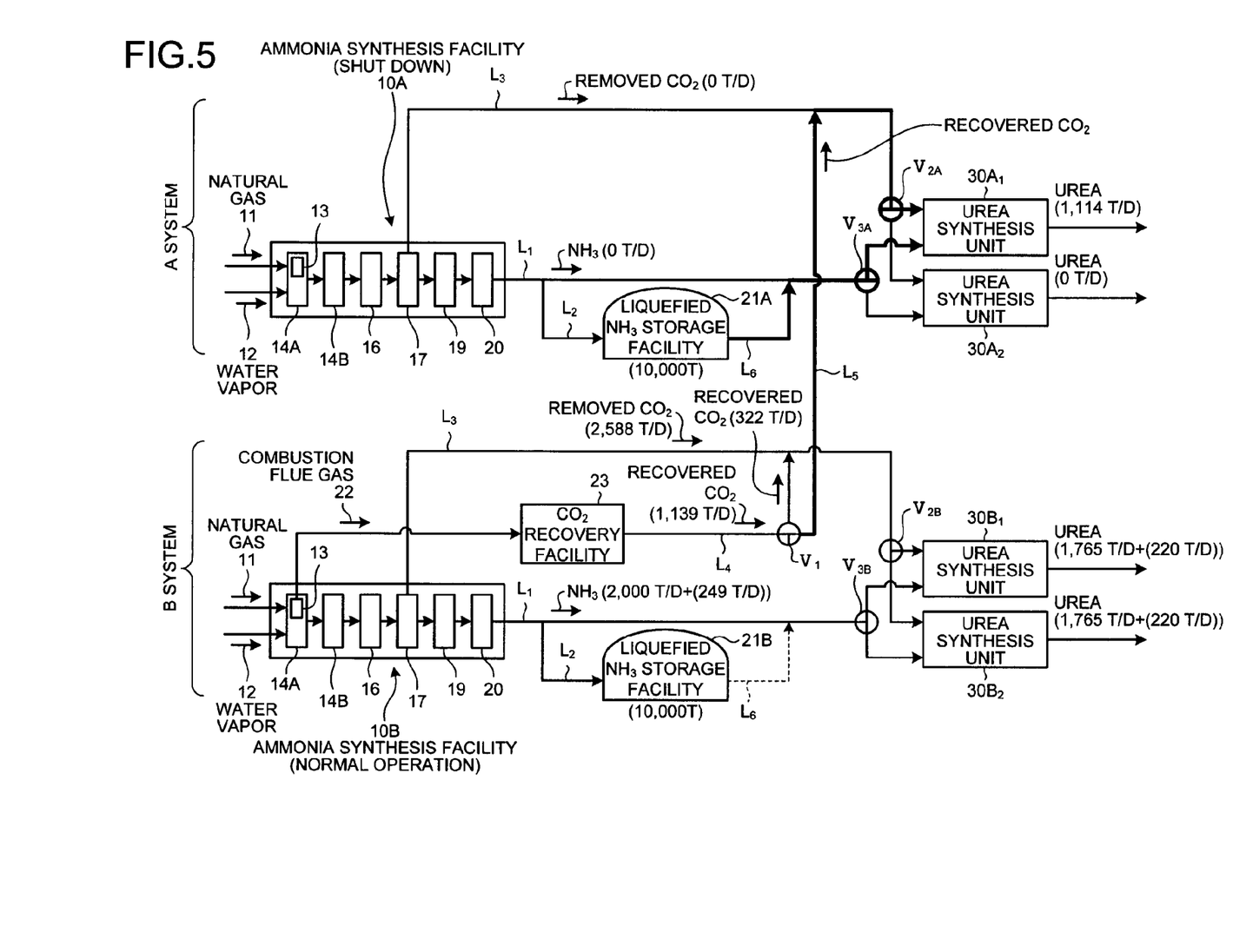
FIG. 5 is a schematic diagram of the urea production plant including multiple systems according to the first embodiment with a production amount added thereto (in a state where one system is shut down).

A continuous urea production amount when the ammonia synthesis facility of the A system is shut down is shown in FIG. 5.

Even if the A system is shut down, the B system can continue normal production, thereby enabling to produce urea in an amount of 3,970 T/D.

Further, recovered $CO_2$ is supplied to the A system along with the supply of liquefied ammonium, thereby enabling to produce urea in an amount of 1,114 T/D.

As a result, conventionally, when the A system is shut down, the urea production amount is only 3,970 T/D by the B system. However, because urea in an amount of 1,114 T/D can be produced continuously in the A system, a total amount of production becomes 5,084 T/D, and thus a considerable increase in the production amount can be achieved with respect to a case where the A system is shut down (3,970 T/D).

In this manner, according to the present embodiment, when urea is produced from $CO_2$ and ammonia, in a case where at least two systems of the urea production plants are arranged in parallel, when the ammonia synthesis facility 10A of one of the systems is shut down, liquefied ammonia stored in the shut down system is used, the $CO_2$ recovery amount in the $CO_2$ recovery facility 23 in the ammonia synthesis facility 10B of the other system is increased, and the increased recovered $CO_2$ and the liquefied ammonia can be used to continue urea synthesis in the urea synthesis unit 30A₁ even in the shut down system.

As a result, the remaining one of the two systems is normally operated to perform urea synthesis, and urea synthesis can be also continued until restart even in the urea production plant of the one system, which has been conventionally shut down, thereby enabling to avoid a considerable decrease in the production amount throughout the year.

At the time of resuming operations of one of the systems after being shut down, because the primary reformer 14A in the ammonia synthesis facility of the A system first starts to operate, even if a device on a downstream side thereof has not yet been operated, $CO_2$ can be recovered from the combustion flue gas 22 of the reforming device 14.

Second Embodiment

Figure 6:
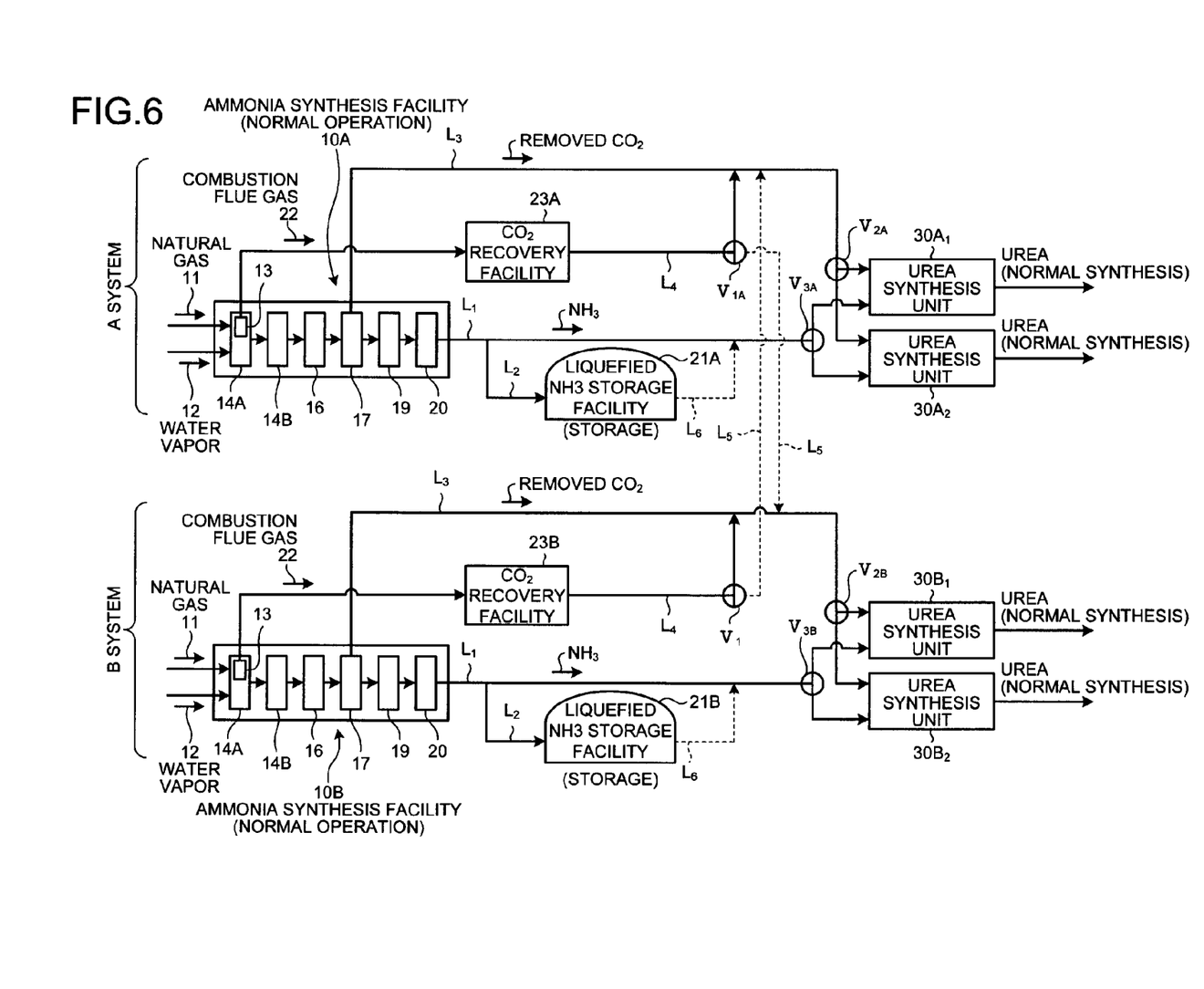
FIG. 6 is a schematic diagram of a urea production plant including multiple systems according to a second embodiment (in a normal operation state).
Figure 7:
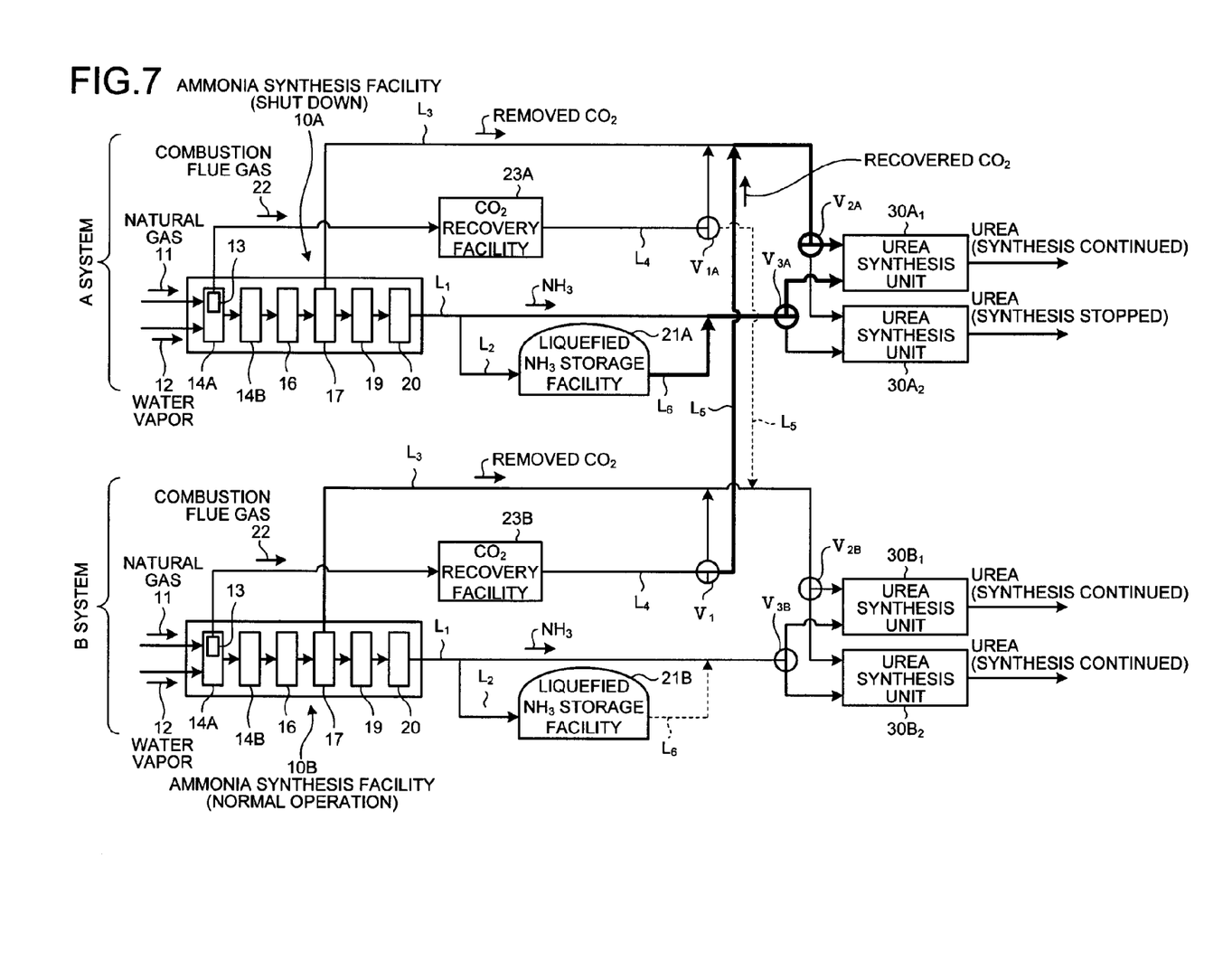
FIG. 7 is a schematic diagram of the urea production plant including multiple systems according to the second embodiment (in a state where one system is shut down).

An operation method of a urea production plant including multiple systems according to a second embodiment of the present invention is explained with reference to the drawings. FIG. 6 is a schematic diagram of the urea production plant including multiple systems according to the second embodiment (in a normal operation state). FIG. 7 is a schematic diagram of the urea production plant including multiple systems according to the second embodiment (in a state where one system is shut down). Constituent elements in the second embodiment that are identical to those in the first embodiment are denoted by like reference signs and explanations thereof will be omitted.

In the first embodiment, the $CO_2$ recovery facility 23 is provided only in the B system; however, in the present embodiment, a $CO_2$ recovery facility 23A is provided in the A system, and a $CO_2$ recovery facility 23B is provided in the B system.

According to the present embodiment, in both the A system and the B system, when the ammonia synthesis facility 10A or 10B is shut down, the both systems can complement each other.

In FIG. 7, recovered $CO_2$ is temporarily supplied to the removed $CO_2$ supply line $L_3$ of the A system from the B system via the emergency $CO_2$ supply line $L_5$ for supplying recovered $CO_2$ (the thick line $L_5$ in FIG. 7).

On the other hand, in an opposite case where the B system is shut down, recovered $CO_2$ can be temporarily supplied to the removed $CO_2$ supply line $L_3$ of the B system from the A system via the emergency $CO_2$ supply line $L_5$ for supplying recovered $CO_2$ (the dotted line $L_5$ in FIG. 7).

As a result, the both systems can complement each other.

Third Embodiment

Figure 8:
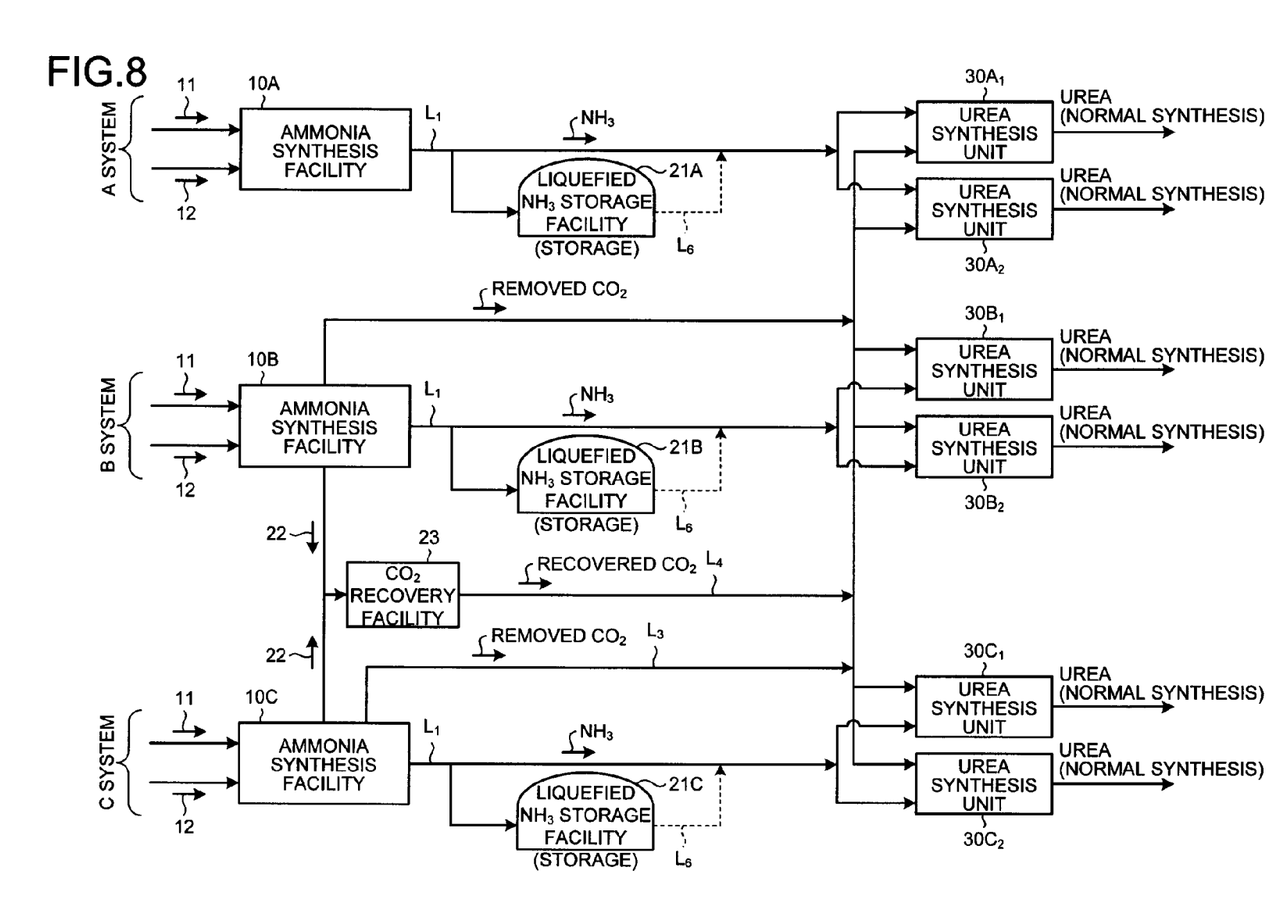
FIG. 8 is a schematic diagram of a urea production plant including multiple systems according to a third embodiment (in a normal operation state).
Figure 9:
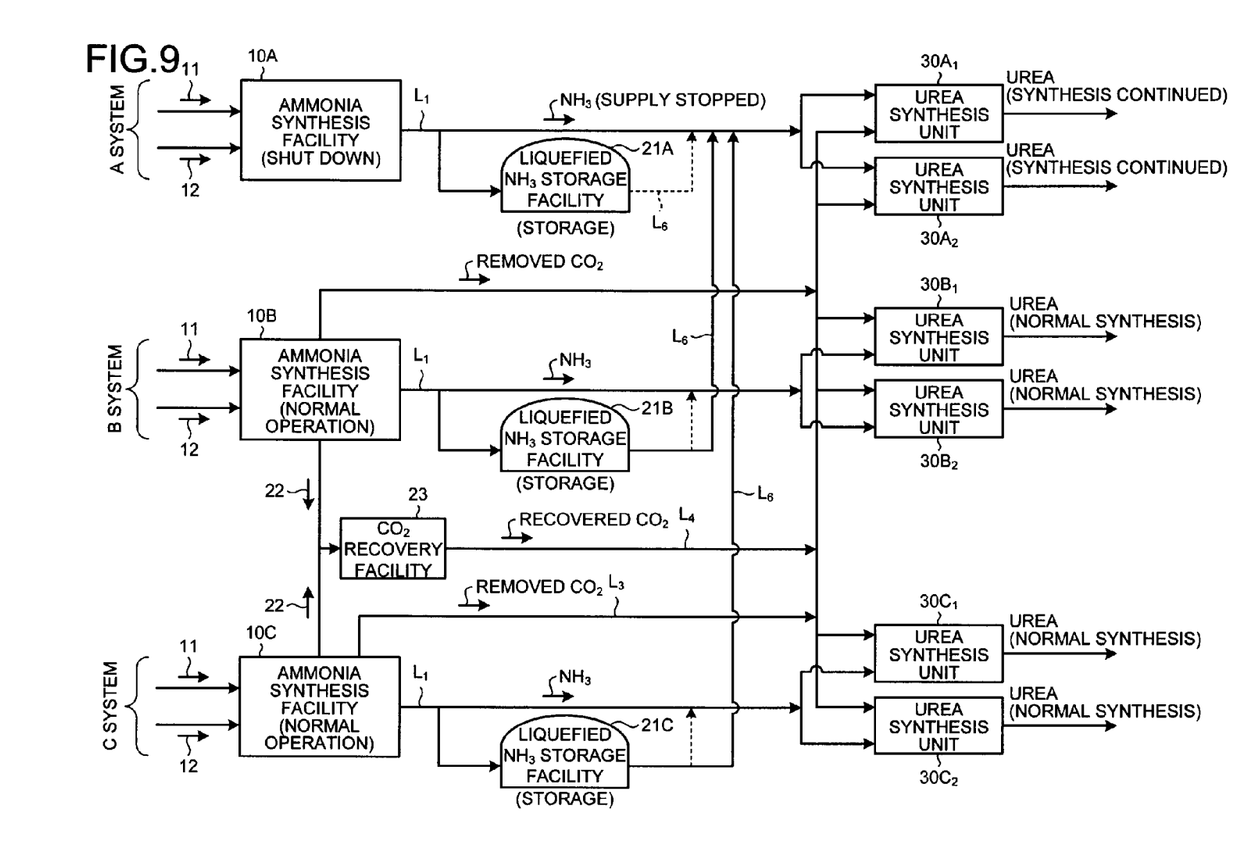
FIG. 9 is a schematic diagram of the urea production plant including multiple systems according to the third embodiment (in a state where one system is shut down).

An operation method of a urea production plant including multiple systems according to a third embodiment of the present invention is explained with reference to the drawings. FIG. 8 is a schematic diagram of the urea production plant including multiple systems according to the third embodiment (in a normal operation state). FIG. 9 is a schematic diagram of the urea production plant including multiple systems according to the third embodiment (in a state where one system is shut down). Constituent elements in the third embodiment that are identical to those in the first embodiment are denoted by like reference signs and explanations thereof will be omitted.

In the first embodiment, the $CO_2$ recovery facility 23 is provided only in the B system; however, in the present embodiment, three systems (A to C systems) are arranged, and a $CO_2$ recovery facility 23 that recovers $CO_2$ in the combustion flue gas 22 from the B system and the C system is provided.

In the present embodiment, because recovered $CO_2$ recovered by the $CO_2$ recovery facility 23 is supplied to each of the urea synthesis units $30A_1$, $30A_2$, $30B_1$, $30B_2$, $30C_1$, and $30C_2$, even if any of the ammonia synthesis facilities 10A to 10C is shut down in the A to C systems, these systems can complement each other.

Fourth Embodiment

Figure 10:
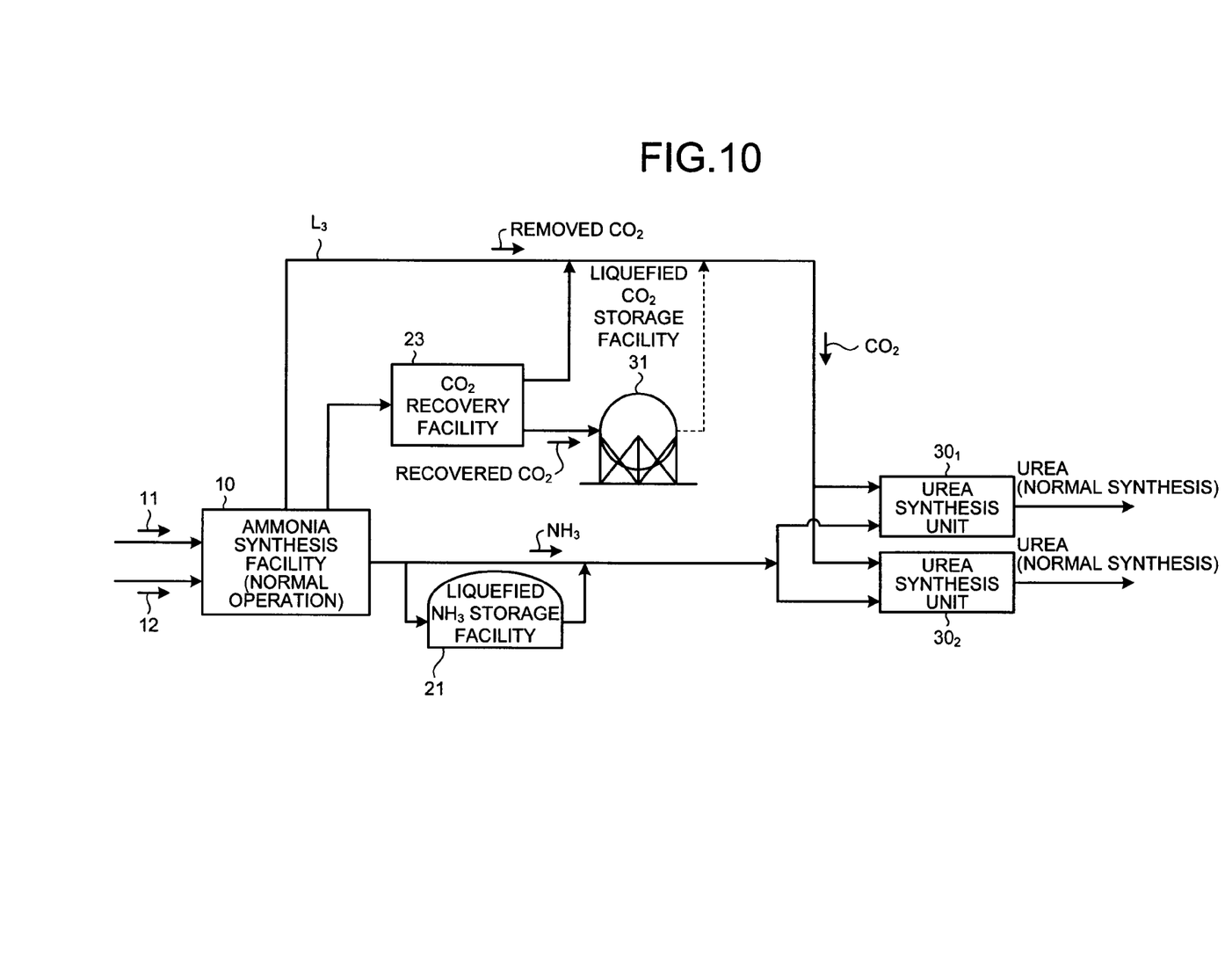
FIG. 10 is a schematic diagram of a urea production plant including multiple systems according to a fourth embodiment (in a normal operation state).
Figure 11:
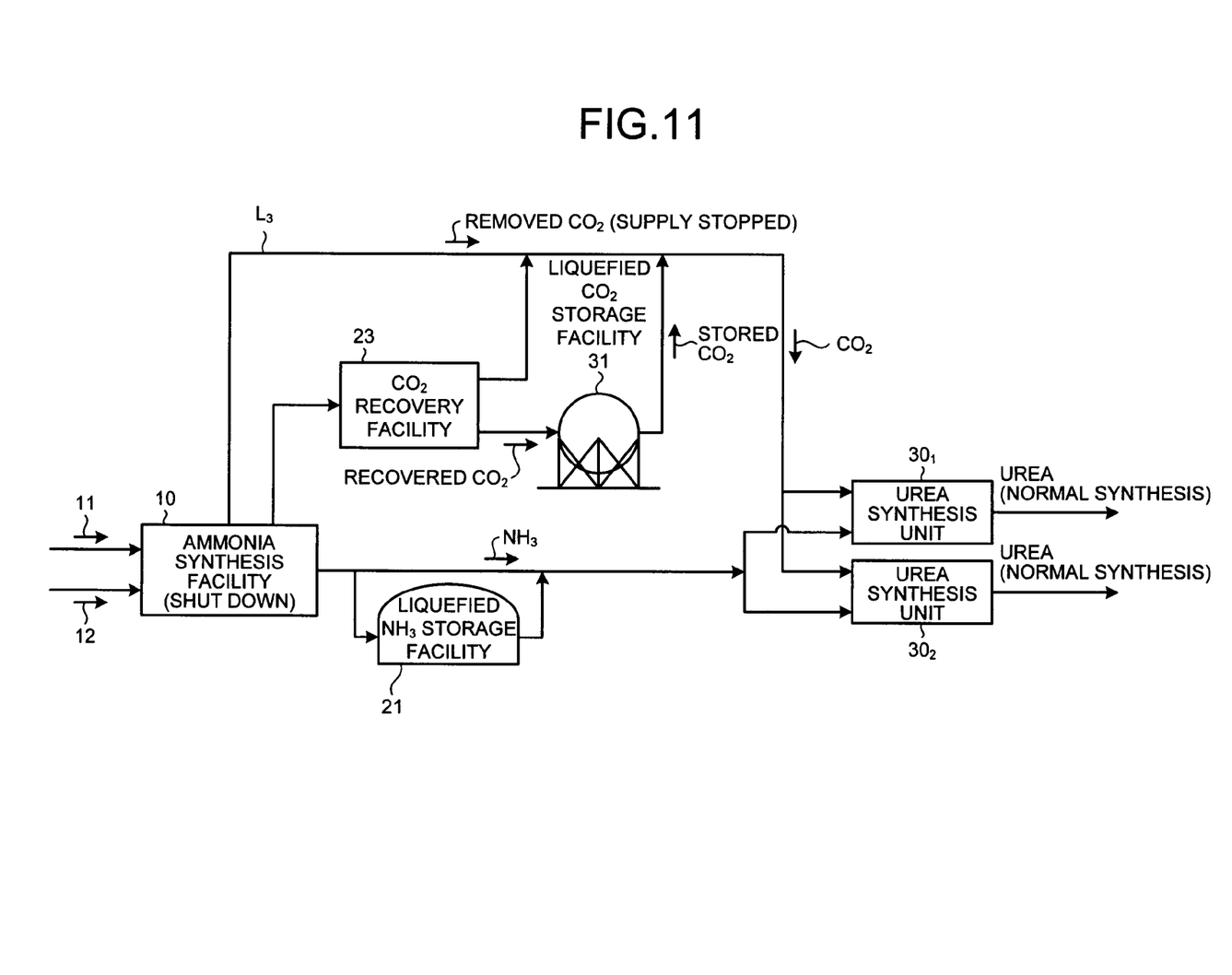
FIG. 11 is a schematic diagram of the urea production plant including multiple systems according to the fourth embodiment (in a shut down state).

An operation method of a urea production plant including multiple systems according to a fourth embodiment of the present invention is explained with reference to the drawings. FIG. 10 is a schematic diagram of the urea production plant including multiple systems according to the fourth embodiment (in a normal operation state). FIG. 11 is a schematic diagram of the urea production plant including multiple systems according to the fourth embodiment (in a shut down state). Constituent elements in the fourth embodiment that are identical to those in the first embodiment are denoted by like reference signs and explanations thereof will be omitted.

In the first embodiment, a case where the ammonia synthesis facility is shut down in multiple systems has been explained. However, in the present embodiment, even when the ammonia synthesis facility in one system is shut down, urea production can be performed.

As shown in FIG. 10, a liquefied $CO_2$ storage facility 31 is provided on a downstream side of the $CO_2$ recovery facility 23, so that recovered $CO_2$ recovered by the $CO_2$ recovery facility 23 is liquefied and stored.

As a result, even when the ammonia synthesis facility 10 is shut down, the stored $CO_2$ from the liquefied $CO_2$ storage facility 31 can be used to continue urea production in the urea synthesis units $30_1$ and $30_2$.

Furthermore, in the present embodiment, the recovered $CO_2$ liquefied and stored is used. However, $CO_2$ in combustion flue gas discharged from an external plant other than the ammonia production facility can be recovered separately by a $CO_2$ recovery device, and the recovered $CO_2$ can be supplied from outside to the urea synthesis unit.

REFERENCE SIGNS LIST 10, 10A to 10C ammonia synthesis facility
11 natural gas
12 water vapor
13 reforming furnace
14 reforming device
15 reformed gas
16 CO-shift converter
17 carbon-dioxide removal device
18 synthesis material gas
19 synthesis gas compressor
20 ammonia synthesis reactor
$30A_1$, $30A_2$, $30B_1$, $30B_2$, $30C_1$, $30C_2$ urea synthesis unit

The invention claimed is:

1. An operation method of at least two urea synthesis plants, each of the at least two urea synthesis plants including:
   an ammonia synthesis facility including a reforming device having a reforming furnace that reforms natural gas to hydrogen ($H_2$) and carbon monoxide (CO) by using water vapor, a CO-shift converter that converts carbon monoxide (CO) in reformed gas to carbon dioxide, a carbon-dioxide removal device that removes obtained carbon dioxide ($CO_2$) in the reformed gas, a synthesis gas compressor that compresses synthesis material gas containing hydrogen and nitrogen, from which carbon dioxide has been removed by the carbon-dioxide removal device, and an ammonia synthesis reactor that synthesizes ammonia from compressed synthesis material gas;
   a liquefied ammonia storage facility that branches ammonia obtained by the ammonia synthesis reactor from an ammonia supply line for supplying ammonia to a urea synthesis unit and stores a part of synthesized ammonia in a liquefied state;
   a carbon-dioxide recovery facility that recovers carbon dioxide in fuel flue gas from the reforming furnace; and
   a carbon-dioxide supply line for supplying the removed carbon dioxide (removed $CO_2$) and the recovered carbon dioxide (recovered $CO_2$) to a urea synthesis unit,
   the operation method comprising:
   providing the at least two urea synthesis plants;
   storing a predetermined amount of obtained ammonia in a liquefied state in each of the liquefied ammonia storage facilities;
   when production of ammonia is stopped in the ammonia synthesis facility of one of the at least two urea synthesis plants,
   temporarily supplying carbon dioxide (recovered $CO_2$) recovered by another of the at least two urea synthesis plants to the carbon-dioxide supply line of the one of the at least two urea synthesis plants via an emergency $CO_2$ supply line in order to supply the temporarily supplied $CO_2$ to the urea synthesis unit;
   supplying a predetermined amount of liquefied ammonia stored in the one of the at least two urea synthesis plants from an ammonia supply line to the urea synthesis unit;
   producing urea by using the temporarily supplied $CO_2$ and stored liquefied ammonia even in the one of the at least two urea synthesis plants, thereby enabling to perform a continuous operation when the ammonia synthesis facility of one of the at least two urea synthesis plants is shut down.

* * * * *